United States Patent [19]

Kubota et al.

[11] Patent Number: 5,294,727
[45] Date of Patent: Mar. 15, 1994

[54] METHOD FOR PREPARING TERTIARY HYDROCARBON-SILYL COMPOUNDS

[75] Inventors: Tohru Kubota; Toshinobu Ishihara; Mikio Endo, all of Joetsu, Japan

[73] Assignee: Shin-Etsu Chemical Co., Ltd., Japan

[21] Appl. No.: 974,989

[22] Filed: Nov. 12, 1992

[30] Foreign Application Priority Data

Nov. 13, 1991 [JP] Japan ................... 3-297434
Aug. 25, 1992 [JP] Japan ................... 4-225382

[51] Int. Cl.$^5$ ............................................. C07F 7/08
[52] U.S. Cl. ................................................... 556/480
[58] Field of Search ........................................ 556/480

[56] References Cited

U.S. PATENT DOCUMENTS

| | | | |
|---|---|---|---|
| 1,963,935 | 6/1934 | Carothers et al. | 556/480 X |
| 2,671,795 | 3/1954 | Frisch et al. | 556/480 |
| 2,813,886 | 11/1957 | Ramsden | 260/448.2 |
| 4,059,607 | 11/1977 | Reedy et al. | 260/448.2 |
| 4,593,112 | 6/1986 | Takamizawa et al. | 556/480 |
| 5,068,386 | 11/1991 | Shirahata | 556/480 |

FOREIGN PATENT DOCUMENTS

0405560A3  1/1991  European Pat. Off.

OTHER PUBLICATIONS

Tetrahedron Letters, vol. 30, No. 46, 1989, pp. 6393–6394, A. Shirahata.
Journal of Organic Chemistry, vo. 52, 1987, pp. 2947–2948, Hosomi et al.
Chemical Abstracts, vol. 77, 1972, Columbus, Ohio, Abst. No. 113417, Tamura et al., p. 369.
Chemical Abstracts, vol. 110, 1989, Columbus, Ohio, Abst. No. 173315, Lennon et al., p. 786.

*Primary Examiner*—Paul F. Shaver
*Attorney, Agent, or Firm*—Parkhurst, Wendel & Rossi

[57] ABSTRACT

A method for preparing a tertiary hydrocarbon-silyl compound comprises the step of reacting a grignard reagent represented by the general formula: $R^1MgX^1$ (wherein $R^1$ represents a tertiary hydrocarbon group and $X^1$ is a halogen atom) with a silicon atom-containing compound represented by the general formula: $X^2{}_mR^2{}_nSiH_{4-m-n}$ (wherein $X^2$ is a halogen atom and may be identical to or different from $X^1$; $R^2$ is a monovalent hydrocarbon group; m is 1, 2 or 3; and n is 0, 1 or 2, provided that m+n is not more than 3 and that if n is 2, $R^2$'s may be identical to or different from one another) in an aprotic inert organic solvent in the presence of a copper compound and/or a quaternary ammonium salt. According to this method, the tertiary hydrocarbon-silyl compounds can industrially efficiently and rapidly produced in high yields.

3 Claims, No Drawings

METHOD FOR PREPARING TERTIARY HYDROCARBON-SILYL COMPOUNDS

BACKGROUND OF THE INVENTION

The present invention relates to a method for industrially, efficiently, and easily preparing a tertiary hydrocarbon-silyl compound.

An article (J. Org. Chem., 1954, 43, p.3649) discloses a method for bonding a tertiary hydrocarbon group to a silicon atom in which a tertiary alkyl lithium is used. According to this method, a tertiary alkyl lithium is first prepared and then reacted with a silicon atom containing compound. The preparation of such a tertiary alkyl lithium requires the steps of melting metal lithium having a high melting point on the order of 190° C. and then dispersing the molten lithium in an organic solvent in the form of particles having a diameter of several micrometers to perform alkylation. Delicate care is required for handling metal lithium used in this method because of the very high activity thereof. For this reason, the use of a particular apparatus is required for the preparation of the tertiary alkyl lithium. Moreover, the tertiary alkyl lithium spontaneously ignites by simply exposed to the air and handling of a large amount thereof is accompanied with various disadvantages including high danger.

Under such circumstances, Japanese Patent Provisional Publication No. 60-222492 discloses a method for preparing tertiary hydrocarbon-silyl compounds which does not require the use of a process for preparing such a tertiary alkyl lithium compound.

According to the method of this patent publication, a tertiary hydrocarbon-silyl compound is prepared by reacting a hydrogen halogenosilane, in which hydrogen and halogen atoms are directly bonded to the silicon atom, with a tertiary alkyl Grignard reagent. The tertiary Grignard reagent can be prepared without use of any particular apparatus and does not suffer from the problem of spontaneous ignition. For this reason, the preparation of tertiary hydrocarbon-silyl compound according to this method has been believed to be hopeful.

However, the reaction rate achieved by this method is too late. In particular, it is difficult to complete the reaction when solvents other than ethers are used and, therefore, the production efficiency thereof is substantially low.

SUMMARY OF THE INVENTION

Accordingly, an object of the present invention is to solve the foregoing problems associated with the conventional techniques and more particularly to provide a method for industrially and efficiently preparing a tertiary hydrocarbon-silyl compound which can accelerate the rate of the reaction of a tertiary alkyl Grignard reagent with a hydrogen halogenosilane.

The method for preparing a tertiary hydrocarbon-silyl compound according to the present invention makes use of a copper compound or a quaternary ammonium salt as a catalyst. The use of such a catalyst can accelerate the rate of the reaction of a tertiary alkyl Grignard reagent with a hydrogen halogenosilane and permit the completion of the reaction and industrially efficient production of the intended tertiary hydrocarbon-silyl compound.

DETAILED EXPLANATION OF THE INVENTION

In the method for preparing a tertiary hydrocarbons-silyl compound according to the present invention, a Grignard reagent represented by the general formula: $R^1MgX^1$ is reacted with a silicon atom-containing compound represented by the general formula: $X^2{}_m R^2{}_n SiH_{4-m-n}$ in an aprotic inert organic solvent in the presence of a copper compound and/or a quaternary ammonium salt. In the foregoing general formulae, $R^1$ represents a tertiary hydrocarbon group; $X^1$ is a halogen atom; $X^2$ is also a halogen atom and may be identical to or different from $X^1$; $R^2$ is a monovalent hydrocarbon group; m is 1, 2 or 3; and n is 0, 1 or 2, provided that m+n is not more than 3 and that if n is 2, $R^2$'s may be identical to or different from one another.

According to the method of the present invention, tertiary hydrocarbon-silyl compounds represented by the general formula: $X_{m-1} R^1 R^2{}_n SiH_{4-m-n}$ are prepared.

In the preparation of the foregoing silyl compounds, a Grignard reagent represented by the formula: $R^1MgX^1$ wherein $R^1$ is a tertiary hydrocarbon group such as t-butyl group, 1,1-dimethylpropyl group or 1,1-diethylpropyl group, or the tertiary hydrocarbon group: $R^1$ may be an alkyl group substituted with an aryl group such as 1,1-dimethyl-2-phenylethyl group and $X^1$ is a halogen atom such as a chlorine or bromine atom.

Specific examples of such Grignard reagents include t-butyl magnesium chloride, t-butyl magnesium bromide, 1,1-dimethylpropyl magnesium chloride, 1,1-diethylpropyl magnesium chloride and 1,1-dimethyl-2-phenylethyl magnesium chloride.

On the other hand, the silicon atom-containing compounds to be reacted with the foregoing tertiary hydrocarbon group-containing Grignard reagent are those represented by the general formula: $X^2{}_m R^2{}_n SiH_{4-m-n}$ wherein $R^2$ is an alkyl group such as a methyl, ethyl or propyl group, an alkenyl group such as a vinyl or allyl group, an aryl group such as a phenyl group, or one of the foregoing groups in which a part or whole of the hydrogen atoms bonded to carbon atoms are substituted with silyl ether group, pyranyl ether group and/or halogen atoms; and $X^2$ is a halogen atom such as a chlorine or bromine atom.

Specific examples of such silicon atom-containing compounds are trichlorosilane, methyldichlorosilane, dimethylchlorosilane, methylchlorosilane, ethyldichlorosilane, phenyldichlorosilane and chloromethyldichlorosilane.

When the foregoing compounds are reacted according to the method of the present invention, a copper compound and/or a quaternary ammonium salt are used as catalysts. Examples thereof include copper salts such as cuprous chloride, cupric chloride, cuprous bromide, cupric bromide, copper iodide and copper cyanide, and complex compounds of copper such as $Li_2CUCl_4$ and $LiCu(CN)Cl$ for the copper compounds; and tetrabutylammonium chloride, tetrabutylammonium bromide, tri-n-octylmethylammonium chloride and tetramethylammonium sulfate for the quaternary ammonium salts. These compounds may be used alone or in any combination.

The amount of the catalyst used ranges from 0.1 to 10 mole % and preferably 0.5 to 5 mole % on the basis of the amount of the foregoing silicon atom-containing compound.

The reaction of the Grignard reagent with the silicon atom-containing compound is carried out in an aprotic inert organic solvent. Examples of such organic solvents usable in the reaction include ether type solvents such as diethyl ether and tetrahydrofuran; and hydrocarbon type solvents such as hexane, toluene and xylene. These organic solvents may be used alone or in any combination thereof, i.e., in the form of a mixture thereof. Particularly preferred are ether-type organic solvents such as tetrahydrofuran since they permit the completion of the reaction within a short period of time at room temperature and consequently lead to reduction of production time and energy-cost. The use of a mixture of a hydrocarbon, type solvent such as xylene with an ether type solvent leads to substantial reduction of the amount of the ether type solvents which are high quality, but expensive and this in turn results in a decrease of production cost.

In the method of the present invention, it is further preferred to add iodine to these organic solvents used in the foregoing reaction.

The reaction temperature in general ranges from 10° to 150° C. and preferably 40° to 100° C. The reaction is preferably carried out in an inert gas atmosphere such as nitrogen or argon. The presence of oxygen in the reaction system becomes a cause of reduction in the yield of the intended reaction product since it reacts with the Grignard reagent.

According to the present invention, the intended product, i.e., the tertiary hydrocarbon-silyl compounds represented by the general formula: $X_{m-1}R^1R^2_nSiH_{4-m-n}$ can be obtained through the reaction explained above.

The present invention will hereinafter be described in more detail with reference to the following non-limitative working Examples.

EXAMPLE 1

To a 500 ml volume flask, there were added 12.2 g (0.5 mole) of metal magnesium, 300 ml of tetrahydrofuran and a small amount of iodine, followed by dropwise addition of 46.3 g (0.5 mole) of t-butyl chloride at a temperature of 40° to 50° C. over one hour in a nitrogen gas atmosphere and subsequent stirring at 55° C. for one hour to give a solution of t-butyl magnesium chloride as a Grignard reagent.

Then 0.72 g (5 mM) of copper bromide was added to the solution of the Grignard reagent, followed by dropwise addition of 57.5 g (0.5 mole) of methyldichlorosilane at room temperature over one hour and subsequent stirring for one hour. The resulting product was examined by the gas chromatography method. As a result, it was found that the methyldichlorosilane was converted into t-butylmethylchlorosilane at a conversion of approximately 100%. The resulting reaction solution was filtered under reduced pressure and then distilled to give a distillate boiling at the temperature range of from 85° to 95° C. Thus, 50.6 g of t-butylmethylchlorosilane was produced. The yield thereof was 74%.

Comparative Example 1

A Grignard reagent was prepared in the same manner used in Example 1 and then the same procedures used in Example 1 were repeated to react the Grignard reagent with methyldichlorosilane except that copper bromide was not used. The resulting product was analyzed by the gas chromatography technique and the rate of conversion of methyldichlorosilane into t-butylmethylchlorosilane was found to be 26%.

Example 2

Tert-butyl magnesium chloride as a Grignard reagent was prepared in the same manner used in Example 1 except that 150 ml of tetrahydrofuran was substituted for 300 ml thereof used in Example 1.

Then 150 ml of xylene and 0.72 g (5 Mm) of copper bromide were added to the Grignard reagent, 57.5 g (0.5 mole) of methyldichlorosilane was dropwise added to the mixture over one hour at room temperature, followed by stirring under reflux for one hour. The rate of conversion of methyldichlorosilane into t-butylmethylchlorosilane was determined by the gas chromatography technique and was found to be 99%. The resulting reaction solution was filtered under reduced pressure and then distilled to give a distillate boiling at the temperature range of from 85° to 95° C. Thus, 47.8 g of t-butylmethylchlorosilane was produced. The yield thereof was 70%.

Comparative Example 2

A Grignard reagent was prepared in the same manner used in Example 2 and then the same procedures used in Example 2 were repeated to react the grignard reagent with methyldichlorosilane except that copper bromide was not used. The rate of conversion of methyldichlorosilane into t-butylmethylchlorosilane was determined by the gas chromatography technique and was found to be 77%.

Example 3

A Grignard reagent was prepared in the same manner used in Example 2 and then the same procedures used in Example 2 were repeated to react the Grignard reagent with methyldichlorosilane except that 1.6 g (5 Mm) of tetra-n-butylammonium bromide was substituted for the copper bromide used in Example 2. The rate of conversion of methyldichlorosilane into t-butylmethylchlorosilane was determined by the gas chromatography technique and was found to be 99%. The resulting reaction solution was filtered under reduced pressure and then distilled to give a distillate boiling at the temperature range of from 85° to 95° C. Thus, 45.8 g of t-butylmethylchlorosilane was produced. The yield thereof was 67%.

Example 4

A Grignard reagent was prepared in the same manner used in Example 1. Then 0.49 g (5 mM) of copper chloride was added to the Grignard reagent followed by dropwise addition of 67.7 g (0.5 mole) of trichlorosilane over one hour at room temperature and stirring for one hour. The resulting product was examined by the gas chromatography technique and it was found that the trichlorosilane was converted into t-butyldichlorosilane in a conversion rate of approximately 100%. The resulting reaction solution was filtered under reduced pressure and then distilled to give a distillate boiling at the temperature range of from 115° to 125° C. Thus, 44.0 g of t-butyldichlorosilane was produced. The yield thereof was 56%.

Example 5

A Grignard reagent was prepared in the same manner used in Example 1. Then 0.72 g (5 Mm) of copper bromide was added to the Grignard reagent followed by dropwise addition of 47.3 g (0.5 mole) of dimethylchlorosilane over one hour at room temperature and stirring for one hour. The rate of conversion of the dimethylchlorosilane into t-butyldimethylsilane was examined by the gas chromatography technique and found to be 99%. Water was added to the resulting reaction solution to remove the tetrahydrofuran through extraction and then distilled to give a distillate boiling at the temperature range of from 85° to 87° C. Thus, 49.3 g of t-butyldimethylsilane was produced. The yield thereof was 84.8%.

Comparative Example 3

The same procedures used in Example 5 were repeated except that copper bromide as a catalyst was not used and the rate of conversion of the dimethylchlorosilane into t-butyldimethylsilane was examined by the gas chromatography technique and found to be 8%.

The results obtained in Examples 1 to 5 and Comparative Examples 1 to 3 clearly indicate that the tertiary hydrocarbon-silyl compounds can be rapidly produced in high yields if Grignard reagents and silicon atom-containing compounds are reacted in the presence of a copper compound and/or a quaternary ammonium salt.

What is claimed is:

1. A method for preparing a tertiary hydrocarbon-silyl compound of the formula $$X_{m-1}R^1R^2{}_n SiH_{4-m-n}$$

wherein
X is a halogen atom;
$R^1$ is a tertiary hydrocarbon group;
$R^2$ is a monovalent hydrocarbon group;
m is 1, 2, or 3; and
n is 0, 1, or 2, with the provisos that m+n is not more than 3 and if n is 2, the two $R^2$s may be the same or different, the method comprising
reacting a Grignard reagent of the formula $$R^1MgX^1$$

wherein
$R^1$ is as previously defined and
$X^1$ is a halogen atom which may be the same as or different from X with a silicon-atom containing compound of the formula $$X_m R^2{}_n SiH_{4-m-n}$$

wherein X, $R^2$, m and n are as previously defined
in an aprotic solvent
in the presence of a catalytic amount of a catalyst selected from the group consisting of a copper compound and a quaternary ammonium salt.

2. The method of claim 1 wherein the copper compound is selected from the group consisting of cuprous chloride, cupric chloride, cuprous bromide, cupric bromide, copper iodide, copper cyanide, $Li_2CuCl_4$, and $LiCu(CN)Cl$.

3. The method of claim 1 wherein the quaternary ammonium salt is selected from the group consisting of tetrabutylammonium chloride, tetrabutylammonium bromide, tri-n-octylmethylammonium chloride, and tetramethylammonium sulfate.

* * * * *